United States Patent [19]
Stowell

[11] Patent Number: 6,107,507
[45] Date of Patent: Aug. 22, 2000

[54] FORMATION OF OLIGOMERIC ORGANOPHOSPHORUS COMPOSITIONS WITH IMPROVED COLOR

[75] Inventor: Jeffrey K. Stowell, Ramsey, N.J.

[73] Assignee: Akzo Nobel NV, Arnhem, Netherlands

[21] Appl. No.: 09/393,870

[22] Filed: Sep. 10, 1999

[51] Int. Cl.[7] .................................. C07F 9/09; C07F 9/40
[52] U.S. Cl. ........................ 558/113; 558/164; 558/165
[58] Field of Search ............................................. 558/113

[56] References Cited

U.S. PATENT DOCUMENTS

| | | |
|---|---|---|
| 2,909,559 | 10/1959 | Lanham . |
| 3,099,676 | 7/1963 | Lanham . |
| 4,382,042 | 5/1983 | Hardy et al. . |
| 5,608,100 | 3/1997 | Sicken ...................................... 558/164 |
| 5,728,746 | 3/1998 | Sicken ...................................... 521/169 |

FOREIGN PATENT DOCUMENTS 812390   4/1959   United Kingdom .

*Primary Examiner*—Michael G. Ambrose
*Attorney, Agent, or Firm*—Richard P. Fennelly

[57] ABSTRACT

An aryl group containing phosphite, such as triphenyl phosphite, can be added to a reaction mixture comprising an organophosphorus compound, phosphorus pentoxide and an alkylene oxide, optionally in the presence of a reagent for the incorporation of hydroxy functionality in the final product. The aryl group containing phosphite is employed to improve the color characteristics of the resulting oligomeric organophosphorus composition.

9 Claims, No Drawings

FORMATION OF OLIGOMERIC ORGANOPHOSPHORUS COMPOSITIONS WITH IMPROVED COLOR

BACKGROUND OF THE INVENTION

The present invention relates to the formation of an oligomeric organophosphorus composition (e.g., a phosphate or phosphonate) by the addition of a novel additive for the color improvement of the resulting product.

It is known to form oligomeric organophosphorus compositions by the reaction of an organophosphorus compound (e.g., a pentavalent phosphorus ester), phosphorus pentoxide and an alkylene oxide. Optionally, a reagent (e.g., water, an alcohol, glycol, or pentaerythritol) is also used to confer hydroxy functionality to the final product. The final compositions include those containing phosphate and/or phosphonate moieties. A representative example of such a process, in which oligomeric orthophosphates are produced, is described in U.S. Pat. No. 4,382,042 to T. A. Hardy et al. In this patent, the use of small amounts (0.01 wt % to 5 wt %) of either an alkyl group-containing or haloalkyl group-containing phosphites is described. Such additives are employed to insure good color characteristics for the resulting product.

More recent U.S. Pat. No. 5,608,100 to M. Sicken describes the formation of oligomeric phosphoric acid esters carrying hydroxyalkoxy groups in which the reaction media contains a similarly small (0.1 wt % to 2 wt %) amount of phosphorous acid.

SUMMARY OF THE INVENTION

Oligomeric organophosphorus compositions, which may contain phosphate and/or phosphonate groups, optionally also containing hydroxyalkyl substitution, and which are made by the reaction of an organophosphorus compound, phosphorus pentoxide and an alkylene oxide (optionally with a reagent producing hydroxyalkyl substitution therein), can have their color improved by conducting such a reaction in the presence of an effective amount of a aryl group-containing phosphite, such as triphenyl phosphite.

DESCRIPTION OF THE PREFERRED EMBODIMENTS

The general process that can be used to make the oligomeric organophosphorus compositions to which the current invention pertains is known in the art. It involves the reaction of an organophosphorus compound, phosphorus pentoxide and an alkylene oxide and is described in detail in the following representative patents which are incorporated herein by reference: U.S. Pat. Nos. 3,695,925 and 4,382,042.

In an exemplary procedure of this type, the initial reaction medium that is formed comprises a selected organophosphorus compound, such as a trialkyl phosphate or a dialkyl alkylphosphonate, with a selected amount of aryl group-containing phosphite (from about 0.01 wt % to about 5 wt %, based on the amount of organophosphorus compound). Then, phosphorus pentoxide is added to react with the selected organophosphorus compound followed by an additional amount of phosphite (from about 0.01 wt % to about 5 wt %, based on the amount of phosphorus pentoxide). Finally, the alkylene oxide (e.g., ethylene oxide) is added.

In the broadest embodiment of the foregoing process, the selected aryl group-containing phosphite is used in an effective amount (from about 0.01 wt % to about 5 wt %, based on the amount of final product) to reduce the level of undesired color in the oligomeric product which is produced. The level of phosphite needed will, in general, increase as one increases the level of phosphorus pentoxide that is employed in the reaction. The aryl group-containing phosphite employed can be a monoaryl dialkyl phosphite, a diaryl monoalkyl phosphite, a triaryl phosphite, or mixtures thereof. In general, both unsubstituted or substituted (e.g., alkyl substituted) alkyl or aryl groups can be employed. The alkyl group (either base alkyl group or substituent can range from one to about ten carbon atoms in size. The preferred triaryl phosphite species for use is triphenyl phosphite. An example of another triaryl species is trinonylphenyl phosphite.

The present invention is further illustrated by the Examples that follow.

COMPARATIVE EXAMPLE 1

This Example illustrates the prior art technology in the manufacture of FYROL 51 flame retardant, which is commercially available from Akzo Nobel Chemicals Inc.

A reactor equipped with an agitator, thermometer, gas inlet, and reflux condenser was charged with 284 g of dimethyl methylphosphonate and 13 g of triethyl phosphite. The solution was warmed to 50° C., and 284 g of phosphorus pentoxide was added, with the exclusion of moisture and air. The slurry was then heated to 110° C. until no further reaction was observed. After cooling the reaction mixture to 50° C., 13 g of triethyl phosphite was again added to the reaction mixture. After phosphite addition, ethylene oxide was introduced into the reaction mixture until no further reaction was observed. This was indicated by a strong reflux of ethylene oxide on a dry ice condenser. Then, 56 g of ethylene glycol was added, and the addition of ethylene oxide continued for an additional twenty hours. Stannous octoate (1 g) was added to the reaction mixture, the temperature was raised to 90° C. and ethylene oxide addition continued until the reaction was complete. The product was then stripped at 50° C. and 5 mm Hg to remove any traces of ethylene oxide, yielding a clear pale amber liquid (APHA=228) with an acid number of 0.6 mg KOH/g. The product had a hydroxyl number of 109 mg KOH/g, and was found to contain 19.5% phosphorus.

EXAMPLE 2

This illustrates the present invention.

An identical reaction sequence to that described in Example 1 was repeated with the following substitution: the two additions of 13 g of triethyl phosphite were replaced with 4.8 g additions of triphenyl phosphite. The product was a clear water white liquid (APHA=22) with an acid number of 0.5 mg KOH/g. The product had a hydroxyl number of 112 mg KOH/g, and was found to contain 19.4% phosphorus.

COMPARATIVE EXAMPLE 3

This Example illustrates the prior art technology in the manufacture of a modified version of FYROL 51 flame retardant, in which ethylene glycol was not used and wherein a lower hydroxy content material was formed.

A reactor equipped with an agitator, thermometer, gas inlet, and reflux condenser was charged with 409 g of dimethyl methylphosphonate and 7.6 g of triethyl phosphite. The solution was warmed to 50° C., and 260 g of phosphorus pentoxide was added, with the exclusion of moisture and air. The slurry was then heated to 85° C. until no further reaction was observed. Ethylene oxide was then introduced into the reaction mixture until no further reaction was observed. This was indicated by a strong reflux of ethylene oxide on a dry ice condenser. Stannous octoate (1.8 g) was added to the reaction mixture, the temperature raised to 100° C. and ethylene oxide addition continued until no further reaction was observed. At this point, 1.8 g of a stannous octoate catalyst was again added to the reaction mixture, with the temperature being raised to 115° C. and ethylene oxide added, until the reaction was complete. The product was then stripped at 50° C. and 5 mm Hg to remove any traces of ethylene oxide, yielding a clear amber liquid (Gardner= 6.5, APHA equivalent about 590) with an acid number of 1.0 mg KOH/g. The product had a hydroxyl number of under 5 mg KOH/g, and was found to contain 23.5% phosphorus.

EXAMPLE 4

This illustrates the present invention.

An identical reaction sequence to that described in Example 3 was repeated with the following substitution: the initial addition of 7.6 g of triethyl phosphite was replaced with a 7.1 g addition of triphenyl phosphite. The product was a clear water white liquid (APHA=22) with an acid number of 1.1 mg KOH/g. The product had a hydroxyl number of under 5 mg KOH/g, and was found to contain 23.4% phosphorus.

COMPARATIVE EXAMPLE 5

This Example illustrates the prior art technology in the preparation of a poly(ethyl ethyleneoxy) phosphate composition.

A reactor equipped with an agitator, thermometer, gas inlet, and reflux condenser was charged with 417 g of triethyl phosphate. The solution was warmed to 50° C., and 217 g of phosphorus pentoxide was added, with the exclusion of moisture and air. The slurry was then heated to 85° C. until no further reaction was observed. Ethylene oxide was then introduced into the reaction mixture until no further reaction was observed. This was indicated by a strong reflux of ethylene oxide on a dry ice condenser. Then, 1.2 g of stannous octoate was added to the reaction mixture, the temperature was raised to 100° C., and ethylene oxide addition continued until no further reaction was observed. A stannous octoate catalyst (1.2 g) was again added to the reaction mixture, and the temperature was raised to 115° C. After eight hours of ethylene oxide addition, an additional 1.2 g of stannous octoate catalyst was added, and the ethylene oxide addition continued until the reaction was complete. The product was then stripped at 50° C. and 5 mm Hg to remove any traces of ethylene oxide, yielding a clear yellow liquid (APHA=170) with an acid number of 1.1 mg KOH/g. The product had a hydroxyl number of under 5 mg KOH/g, and was found to contain 19.3% phosphorus.

COMPARATIVE EXAMPLE 6

This also illustrates use of the prior art technology.

An identical reaction sequence to that described in Example 5 was performed with the following substitution: the initial reactor charge consisted of 417 g of triethyl phosphate and 7.9 g of triethyl phosphite. The product was a clear pale yellow liquid (APHA=105) with an acid number of 1.2 mg KOH/g. The product had a hydroxyl number of under 5 mg KOH/g, and was found to contain 19.2% phosphorus.

EXAMPLE 7

This illustrates use of the present invention.

Another identical reaction sequence to that described in Examples 5 and 6 was performed with the following substitution: the initial reactor charge consisted of 417 g of triethyl phosphate and 4.7 g of triphenyl phosphite. The product was a clear water white liquid (APHA=29) with an acid number of 1.0 mg KOH/g. The product had a hydroxyl number of under 5 mg KOH/g, and was found to contain 19.2% phosphorus.

The foregoing Examples should not be construed in a limiting fashion since they are merely presented to illustrate certain embodiments of the present invention. The scope of protection sought is set forth in the Claims that follow.

I claim:

1. In a process for the formation of an oligomeric organophosphorus composition by reaction of an organophosphorus compound, phosphorus pentoxide and an alkylene oxide, optionally in the presence of a reagent for the incorporation of hydroxy functionality, the improvement comprising the presence during such reaction of an effective amount of an aryl group-containing phosphite to improve the color characteristics of the resulting oligomeric organophosphorus composition.

2. A process as claimed in claim 1 wherein the organophosphorus compound is a trialkyl phosphate.

3. A process as claimed in claim 1 wherein the organophosphorus compound is a trialkyl phosphate and the alkylene oxide is ethylene oxide.

4. A process as claimed in claim 1 wherein the organophosphorus compound is a trialkyl phosphate and the aryl group-containing phosphite is triphenyl phosphite.

5. A process as claimed in claim 1 wherein the organophosphorus compound is a trialkyl phosphate, the alkylene oxide is ethylene oxide, and the aryl group-containing phosphite is triphenyl phosphite.

6. A process as claimed in claim 1 wherein the organophosphorus compound is a dialkyl alkylphosphonate.

7. A process as claimed in claim 1 wherein the organophosphorus compound is a dialkyl alkylphosphonate and the alkylene oxide is ethylene oxide.

8. A process as claimed in claim 1 wherein the organophosphorus compound is a dialkyl alkylphosphonate and the aryl group-containing phosphite is triphenyl phosphite.

9. A process as claimed in claim 1 wherein the organophosphorus compound is a dialkyl alkylphosphonate, the alkylene oxide is ethylene oxide, and the aryl group containing phosphite is triphenyl phosphite.

* * * * *